(12) United States Patent
Peng et al.

(10) Patent No.: US 10,987,318 B2
(45) Date of Patent: Apr. 27, 2021

(54) APPLICATION OF CLOFOCTOL FOR MANUFACTURING PHARMACEUTICAL PRODUCT FOR TREATING HUMAN NEUROGLIOMA

(71) Applicant: INSTITUTE OF BASIC MEDICAL SCIENCES, CHINESE ACADEMY OF MEDICAL SCIENCES, Beijing (CN)

(72) Inventors: Xiaozhong Peng, Beijing (CN); Yan Hu, Beijing (CN); Wei Han, Beijing (CN); Boqin Qiang, Beijing (CN)

(73) Assignee: Institute of Medical Sciences, Chinese Academy of Medical Sciences, Beijing (CN)

( * ) Notice: Subject to any disclaimer, the term of this patent is extended or adjusted under 35 U.S.C. 154(b) by 172 days.

(21) Appl. No.: 16/303,138

(22) PCT Filed: Mar. 20, 2017

(86) PCT No.: PCT/CN2017/077346
§ 371 (c)(1),
(2) Date: Nov. 19, 2018

(87) PCT Pub. No.: WO2017/197972
PCT Pub. Date: Nov. 23, 2017

(65) Prior Publication Data
US 2020/0060988 A1    Feb. 27, 2020

(30) Foreign Application Priority Data
May 19, 2016    (CN) .......................... 201610333673.8

(51) Int. Cl.
*A61K 31/05*    (2006.01)
*A61P 35/00*    (2006.01)

(52) U.S. Cl.
CPC .............. *A61K 31/05* (2013.01); *A61P 35/00* (2018.01)

(58) Field of Classification Search
CPC ................................ A61K 31/05; A61P 35/00
See application file for complete search history.

(56) References Cited

U.S. PATENT DOCUMENTS

| 2009/0062227 A1* | 3/2009 | Schonthal | A61N 5/10 514/44 R |
| 2011/0110958 A1* | 5/2011 | Qiu | A61P 35/00 424/174.1 |

FOREIGN PATENT DOCUMENTS

| CN | 105943522 A | 9/2016 |  |
| EP | 1595543 A2 * | 11/2005 | ............. A61K 31/00 |
| WO | 2007/009264 A1 | 1/2007 |  |

OTHER PUBLICATIONS

PCT International Search and Preliminary Examination Guidelines. World Intellectual Property Organization. Published Mar. 2004. (Year: 2004).*
Wang (British Journal of Pharmacology vol. 171 pp. 4478-4489. Published 2014). (Year: 2014).*
Wang et al, (British Journal of Pharmacology vol. 171 pp. 4478-4489. Published 2014). (Year: 2014).*

* cited by examiner

*Primary Examiner* — Theodore R. Howell
*Assistant Examiner* — George W Kosturko
(74) *Attorney, Agent, or Firm* — Rodney J. Fuller; Booth Udall Fuller, PLC

(57) ABSTRACT

The present invention discloses an application of clofoctol for manufacturing a pharmaceutical product for treating human neuroglioma. The clofoctol is a pharmaceutical product for treating an upper respiratory tract infection. The clofoctol exerts a significant and specific inhibition of a glioma stem cell activity relative to a human neuroglioma cell or a normal human astroglia, human embryonic kidney cell, and human neural stem cell. A glioma stem cell treated with the clofoctol exhibited significantly reduced self-renewal, tumorsphere formation, and in vivo tumor formation in a nude rat. In vivo experiments using a zebrafish glioma transplantation model and a nude rat glioma transplantation model provided in vivo verification for the therapeutic efficacy of the pharmaceutical product against glioma. The invention specifically found that a clofoctol for treating an upper respiratory tract infection can achieve targeted inhibition of the glioma stem cell, and can thus be used in preparing a pharmaceutical product for treating human neuroglioma. The invention provides a novel therapeutic pharmaceutical product for treating human neuroglioma.

20 Claims, 8 Drawing Sheets

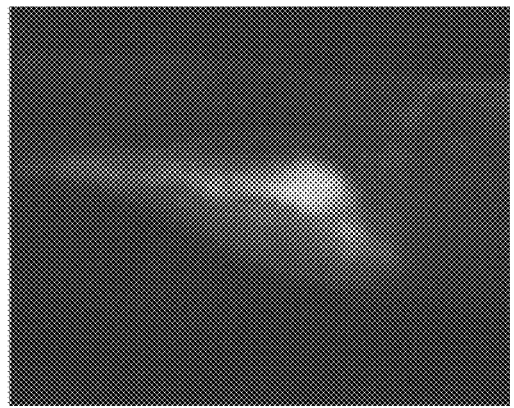
Figure.8A                Figure.8B
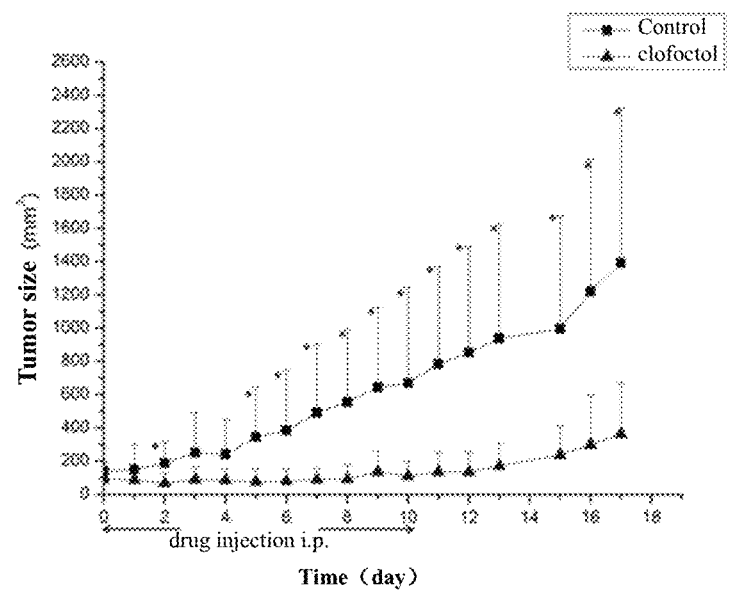
Figure.9A

APPLICATION OF CLOFOCTOL FOR MANUFACTURING PHARMACEUTICAL PRODUCT FOR TREATING HUMAN NEUROGLIOMA

FIELD OF THE INVENTION

The present invention relates to the field of tumor treatment, specifically relates to the use of the clofoctol for the manufacturing of a medicament for the treatment of human neuroglioma.

BACKGROUND OF THE INVENTION

Neuroglioma, derived from the neuroepithelial, is the most common primary intracranial malignancy, which possesses the characteristics of high malignancy, rapid growth, high invasiveness and high morbidity. Although the remarkable progress has been made in current comprehensive treatment techniques for tumor, traditional surgery and radiotherapy cannot completely cure the neuroglioma, resulting in high recurrence rate, high mortality and low cure rate, since neuroglioma is located in an important position of the brain, which accompanied by microvascular proliferation and presenting significant invasive growth. At present, the medicaments for clinical chemotherapy are mainly the alkylating medicaments, however the traditional alkylating agents have strong side effects and are prone to producing drug resistance. Although the new alkylating agent, temozolomide (TMZ), produces low side effect and is well tolerated for long-term administration, the reports on myelodysplastic syndrome (MDS), acute myeloid leukemia (AML), and acute lymphoblastic leukemia (ALL) caused by the TMZ treatment are increasing, the specific reason for which is still under further research. Therefore, there is an urgent need to find a new generation of effective medicaments for the treatment of neuroglioma, so as to improve the treatment of neuroglioma.

In recent years, scientists have made many efforts in the exploration and development of new medicaments for neuroglioma, according to the mechanism of development and progression of neuroglioma. The studies have shown that the development and progression of neuroglioma are mainly related to abnormal expression or mutation of the corresponding key molecules in the RTK/RAS/PI3K pathway, p53 pathway and RB pathway. Therefore, recent studies focus on developing the inhibitors of the corresponding pharmaceutical molecules to counteract the effects of certain key molecules. However, they all show good therapeutic prospects merely in preclinical studies and are not satisfactory or have quite limited effect in the Phase I or Phase II clinical trial, or even after approval. For example, EGFR inhibitors: Gefitinib and Erlotinib have been demonstrated to be prone to induce drug resistance, and such medicaments have therapeutic effect on very few patients. After administration, the progression-free survival was not observed to be extended in all patients. Meanwhile, it has been demonstrated that both the EGFR/Her2 inhibitor Lapatinib and the monoclonal antibody of EGFR Cetuximab have little therapeutic effect on neuroglioma. In addition, it has been demonstrated that the treatment with mTOR-associated inhibitors (Rapamycin, Temsirolimus, Everolimus, Ridaforolimus), Histone deactylase (HDAC) inhibitors (Vorinostat, etc.) alone or in combination with temozolomide has no or little effect. At the same time, in view of the characteristics of microangiogenesis in neuroglioma, the anti-angiogenic molecules such as bevacizumab and cedirib, which have been demonstrated to have partial effects, have been developed in some studies. They can quickly reduce the edema of para-carcinoma, effectively prolong the progression-free survival of patients, but also cannot reverse the progression of the disease. The patients received anti-angiogenic therapies eventually fail to cure successfully, and the present situation that most patients die several months after the diagnosis still cannot be changed. In general, despite the efforts have been made by the domestic and foreign scientists and pharmaceutical companies in the exploration of new medicaments for neuroglioma, no novel and effective pharmaceutical molecules have been found. Due to the complex pathogenesis of glioma, we do not know which key molecules need to be inhibited in the patients with glioma caused by different pathogenesis. In addition, other scientists have suggested that the cells in the glioma tissue are heterogeneous. The reasons for the poor effect of above-mentioned pharmaceutical molecules may be due to the fact that we failed to choose the cell type that plays an important role in the development and progression of glioma.

In 1994, Lapidot et al. for the first time isolated tumor stem cells from patients with leukemia, and the theory of tumor stem cells was gradually accepted. Subsequently, Singh et al. isolated very few of $CD133^+$ glioma stem cells from glioma, which have the abilities of self-renewal and differentiation and have stronger in vivo tumorigenesis ability than that of $CD133^-$ cells. 100 $CD133^+$ glioma stem cells has been enough to induce tumorigenesis in nude mouse. Jian Chen et al. demonstrated the presence of glioma stem cells in vivo by intracellular tracer technology. With the further research, the characteristic and property of glioma stem cell and its relationship with glioma are gradually revealed. Studies have shown that glioma stem cell is the primary cause for the development and progression of glioma, and glioma stem cell can induce tumor angiogenesis by activating Wnt signaling, and induce enhancing tumor hypoxia stress and invasion ability, etc. In addition, Bao et al. confirmed that glioma stem cells can also produce radiotherapy and chemotherapy resistance. After receiving treatment for a period of time, chemotherapeutic medicaments of glioma which only target the entire tumor tissue reduce the tumor tissue of the patients, indicating some certain effect. However, glioma stem cells that are resistant to chemotherapy can further form new tumor tissues through proliferation and differentiation, thereby promoting tumor recurrence. It can be seen that the glioma stem cells are closely related to the development and progression of glioma, to the resistance against radiotherapy and chemotherapy and also related to tumor recurrence, which are the important factor for refractory glioma. Therefore, we envisage whether it is possible to achieve the ultimate elimination of the entire tumor tissue by using medicaments that target glioma stem cells in combination with traditional radiotherapy and chemotherapy.

In recent years, several medicaments that target tumor stem cells for different tumors have been reported by the domestic and foreign scientists, including some novel pharmaceutical molecules and the pharmaceutical molecules which have been used clinically. Using the tumorigenesis model of nude mouse, it was verified that the following medicaments have a better antitumor effect than the current first-line medicament TMZ, such as natural polyphenol resveratrol, ionophore salinomycin and tunicamycin with antimicrobial activity, niclosamide which is a medicament with anti-tapeworm activity and metformin which is used to treat diabetes, as well as sorafenib which is used to treat liver cancer. However, none of the above medicaments can exert a function of targeting tumor stem cells under safety-ensuring condition, and thus the effects thereof are limited.

Clofoctol is an antimicrobial medicament and is mainly used in the treatment of upper respiratory tract as well as ear, nose and throat infections caused by gram-positive bacteria. It is used in France and Italy, and was first approved in France during 1980. The inhibition of gram-positive bacteria by clofoctol may be achieved by inhibiting the synthesis of cell wall and affecting energy metabolism, but without affecting the synthesis of DNA, RNA and protein. The resistance of gram-negative bacteria to clofoctol may be due to its inability to penetrate the outer membrane of gram-negative bacteria. Clofoctol is administrated through oral and rectal suppository (1.5 g per person, daily, the main method of administration) for anal administration. Clinical observations have shown that the side effects of clofoctol are slight, although some patients may have side effects such as maculopapular rash or rectal distension during the use of the medicament. The current reports on clofoctol mainly focus on its inhibition of gram-positive bacteria and the treatment of upper respiratory tract infection. In 2014, an article co-authored by Soochow University and Johns Hopkins Medical University School of Medicine reported that clofoctol could inhibit prostate cancer by inducing endoplasmic reticulum stress, inhibiting cellular protein translation and cell cycle arrest, which revealed the anti-tumor effect of clofoctol.

The present invention finds out that clofoctol has specific inhibitory effects at cellular level on four glioma stem cells isolated in the laboratory, when compared with glioma cells, normal human astrocytes, human embryonic kidney cells, human neural stem cells. In view of this, it is confirmed that clofoctol can specifically inhibit the ability of self-renewal, tumorsphere formation and tumorigenesis of glioma stem cells at the cellular level. Then, zebrafish glioma xenograft model and nude mouse glioma xenograft model are used to demonstrate the therapeutic effect of clofoctol on glioma. Thus, clofoctol will potentially become novel potent therapeutic medicament for the treatment of neuroglioma.

SUMMARY OF THE INVENTION

According to the above-mentioned purposes, the present invention provides the use of clofoctol for manufacturing of a medicament for treatment of human neuroglioma.

In a specific embodiment, said human neuroglioma is treated by said medicament through inhibiting the cell activity of glioma stem cells.

In a preferred embodiment, said human neuroglioma is treated by said medicament through inhibiting the capacities of self-renewal, tumorsphere formation and tumorigenesis in vivo of glioma stem cells.

In a preferred embodiment, said human neuroglioma is treated by said medicament through inducing the apoptosis of glioma stem cells.

In an alternative embodiment, said glioma stem cells comprise, but not limit to U87MG SLC, U251 SLC, GSC2, GSC5.

In an alternative embodiment, said human neuroglioma is treated by said medicament through inhibiting glioma cells.

In an alternative embodiment, said glioma cells comprise, but not limit to U251, U87MG; N3.

In an alternative embodiment, said human neuroglioma is Grade I to IV neuroglioma.

Definition of Terminology

"Glioma stem cells": a tiny minority of cells existing in glioma tissues, possessing self-renewal ability, pluripotency ability, and tumorigenesis ability in vivo, which are closely related to the development and progression, recurrence of glioma and also to the formation of radiotherapy and chemotherapy resistance.

"MTS assay": a colorimetric method for determining the number of viable cells in proliferation assays and cytotoxicity assays. MTS is a novel tetrazolium compound. PMS is an electron coupling reagent with enhanced chemical stability, which forms a stable solution when mixed with MTS. MTS can be reduced by cellular organisms to generate a colored formazan product that is soluble in culture media. This conversion is thought to be carried out by NAD(P)H-dependent dehydrogenase enzymes in metabolically active cells. The amount of the formazan product, which is quantified at 490 nm, is proportional to the number of viable cells in culture.

"The relative cell viability": after the detection of the value of absorbance by above MTS assay, the relative cell viability is calculated based on the value of absorbance (A). The relative cell viability=$(A_{treatment\ group}/A_{control\ group})\times 100\%$.

"Self-renewal" refers to a process that a stem cell (in particular the glioma stem cells herein) produces at least one daughter cell retaining the properties of the stem cell by symmetric or asymmetric division. Self-renewal can maintain the pluripotency of the stem cells. For the tissue-specific stem cells, self-renewal is the basis for the maintenance of their potential for differentiation throughout life time.

"The ability of tumorsphere formation" means the ability of tumor stem cells (in particular the glioma stem cells herein) forming tumorsphere, when cultivated in vitro in a medium containing EGF and bFGF.

From the above, the present invention finds out that the clinical medicament clofoctol can be used for manufacturing of a medicament for the treatment of human neuroglioma, which provides a novel and effective medicament for the treatment of human neuroglioma, showing significant social and economic benefits.

DESCRIPTION OF THE DRAWINGS

FIGS. 3A to 3H show the change in morphology under optical microscope.

FIG. 8A and FIG. 8B: clofoctol significantly inhibits tumor growth in zebrafish glioma xenograft model. 3000 green-fluorescent-labeled U87MG SLC-GFP were injected into the yolk sac of the 48-hour zebrafish embryo, and after 48 hours of natural growth, they were treated with clofoctol at a concentration of 10 µM for 48 hours (FIG. 8B). Fluorescence microscopy was used to detect the intensity of green fluorescence in the yolk sac of zebrafish, so as to determine the anti-tumor effect of clofoctol on zebrafish xenograft model. FIG. 8A shows the control group.

FIG. 9A to FIG. 9C: clofoctol significantly inhibits tumor growth in the nude mouse xenograft model with fewer side effects. GSC2 cells were subcutaneously inoculated into armpits of 15 Balb/C nude mice of 5-weeks old. The inoculated number of cells was $10^5$ cells/mouse. When the subcutaneous tumors in nude mice grew to about 100 mm³, they were divided into DMSO group and clofoctol administration group. The dose administered was 20 mg/kg, the mice were administered by intraperitoneal injection for a period of 11 days. The change of tumor size (FIGS. 9A and 9B) and the body weight (FIG. 9C) in the two groups of nude mice were recorded.

FIG. 10A-1 to FIG. 10A-5: clofoctol can induce apoptosis in glioma stem cells. After the treatment of GSC2 with clofoctol at a concentration of 0 µM (control, FIG. 10A-1), 1 µM (FIG. 10A-2), 3 µM (FIG. 10A-3), 10 µM (FIG. 10A-4), 30 µM (FIG. 10A-5) for 12 hours, the cells were counter-stained with Annexin V/PI, and then the apoptosis of cells in each treatment group was analyzed by flow cytometry. FIG. 10A-1 to FIG. 10A-5 (gate: P2) show that clofoctol can significantly induce apoptosis of glioma stem cells.

FIG. 10B-1 to FIG. 10B-5: clofoctol can induce apoptosis in glioma stem cells. After the treatment of clofoctol at a concentration of 0 µM (control, FIG. 10A-1), 1 µM (FIG. 10A-2), 3 µM (FIG. 10A-3), 10 µM (FIG. 10A-4), 30 µM (FIG. 10A-5) for 24 hours, the cells were counter-stained with Annexin V/PI, and then the apoptosis of cells in each treatment group was analyzed by flow cytometry. FIG. 10B-1 to FIG. 10B-5 (gate: P2) show that clofoctol can significantly induce apoptosis of glioma stem cells.

DETAILED DESCRIPTION OF THE INVENTION

Figure 1:
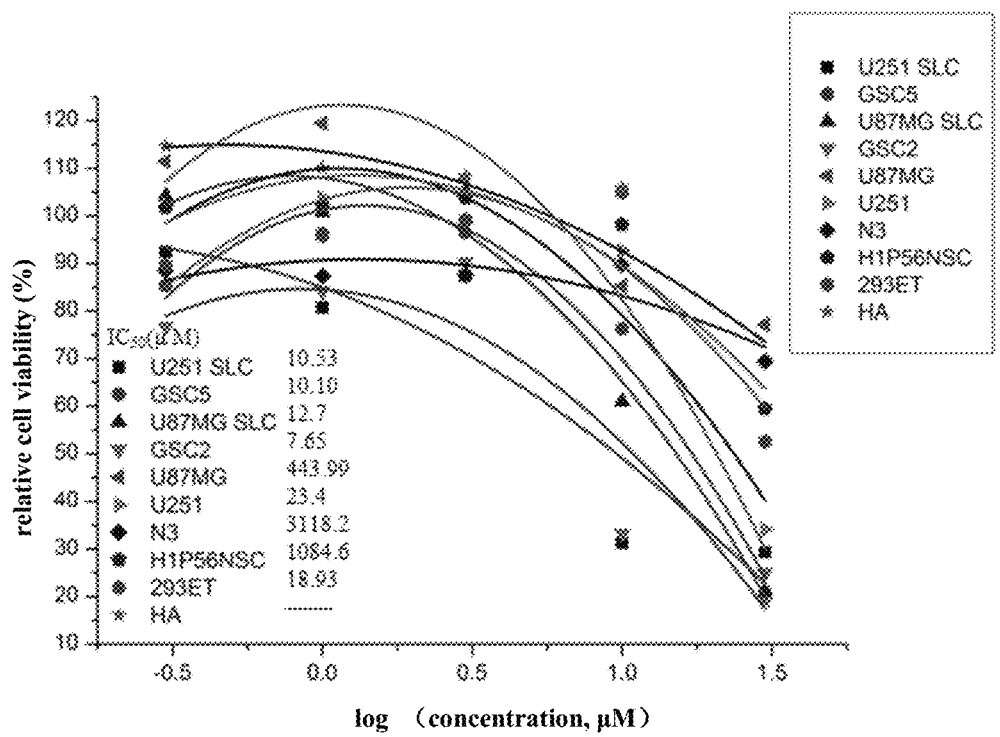
FIG. 1: clofoctol specifically inhibits the cell activity of glioma stem cells. The cell viability of four glioma stem cell lines (U87MG SLC, U251 SLC, GSC2, GSC5), three glioma cell lines (U251, U87MG, N3 (primary glioma cells isolated from patient tumor tissue)) and three normal human cell lines (normal human astrocytes (HA), human neural stem cells (H1p56NSC), human embryonic kidney cells (293ET)) were detected by MTS (tetrazolium compound) assay after 48 hours of clofoctol treatment at different concentrations (0.3 µM, 1 µM, 3 µM, 10 µM, 3004), "--" indicates $IC_{50}$ value>$10^6$ µM.

The invention will be further clarified by the following non-limiting examples. It is known to those skilled in the art that many modifications may be made to the invention without departing from the spirit of the invention. Such modifications are also within the scope of the invention.

The following experimental methods are conventional methods unless otherwise specified, and the experimental materials used can be easily obtained from commercial companies unless otherwise specified.

Example 1: Detection of Cell Viability by MTS Assay (1) Preparing the following solutions according to the manufacturer's instructions:

a. DPBS: 0.2 g of KCl, 8.0 g of NaCl, 0.2 g of $KH_2PO_4$, 1.15 g of $Na_2HPO_4$ were sequentially added to reach 1 L, the pH was adjusted to 7.35, then 0.1 g of $MgCl_2.6H_2O$ was added to the solution. The solution was fully mixed until it became clear, then 0.133 g of $CaCl_2.2H_2O$ was added to the solution, and then the solution was fully mixed until it became clear. After filtration sterilization twice through 0.2 µM filter, the aliquot was stored at 4° C.;

b. Preparation of PMS solution: 0.92 mg/mL PMS solution was prepared using DPBS, and subjected to filtration sterilization twice using 0.2 µM filter, and then the aliquots in EP tubes were wrapped with tinfoil, and stored at −20° C. in the darkness;

c. Preparation of MTS solution: the solution was prepared at the ratio of 1 mg MTS powder in 0.5 mL DPBS, mixed gently for about 15 min, until MTS was completely dissolved. The pH was measured and maintained between 6.0 and 6.5. After filtration sterilization twice using 0.2 μM filter, the aliquots in EP tubes were wrapped with tinfoil, and stored at −20° C. in the darkness;

d. Preparation of MTS/PMS solution: MTS and PMS were respectively thawed and incubated at 37° C. for 15 min. 4.2 mg of MTS powder was dissolved in 2.1 mL of DPBS, and 0.1 mL of PMS was added before use.

(2) In order to detect the effect of clofoctol on cell viability of glioma stem cells, the experiment was carried out using a 96-well cell culture plate which is coated with 100 μg/mL poly-lysine overnight, wherein the plate was washed twice next day with saline, and allowed to dry until use. The cells were digested, resuspended as a single cell suspension, counted and seeded on a 96-well cell culture plate (U87MG SLC (5000 cells/well), U251 SLC (10000 cells/well), GSC2 (10000 cells/well), GSC5 (10000 cells/well)), allowed to grow overnight. Next day, clofoctol (purchased from MicroSource, USA) was added into the well, its chemical formula is shown in Formula I, the chemical molecule formula of clofoctol is $C_{21}H_{26}Cl_2O$, the condensed formula thereof is Clc1cc(Cl)ccc1Cc2cc(ccc2O)C(C)(C)CC(C)(C)C, and the system name is 2-[(2,4-dichlorophenyl)methyl]-4-(2,4,4-trimethylpentan-2-yl)phenol.

The following concentration gradient was set as: 0.3 μM, 1 μM, 3 μM, 10 μM, 30 μM, 3 replicate wells per medicament concentration, the cells were treated for 48 hours.

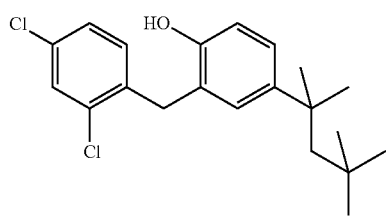

Formula I (3) As to the three glioma cell lines (U251 (purchased from ATCC, U.S.A), U87MG (purchased from ATCC, U.S.A), N3 (primary glioma cells isolated from the patient's tumor tissue, received from Jiang Tao laboratory of Tiantan Hospital), three normal human cell lines (normal human astrocytes (HA, purchased from ATCC, U.S.A), human neural stem cells (H1p56NSC, a cell line established in our laboratory), human embryonic kidney cells (293ET, purchased from Cell Center, Institute of Basic Medical Sciences, Chinese Academy of Medical Sciences)), the 96-well cell culture plate was not coated. The concentration for cell plating was 5000 cells per well. Other operations are as above.

(4) After the treatment with clofoctol for 48 hours, a corresponding volume of MTS/PMS test solution was prepared as needed, and then serum-free culture medium was added at a ratio of test solution:culture medium=1:5. Finally, the system was 120 μL in each well and was incubated for 2 hours at 37° C. in 5% $CO_2$. The read data was obtained at an absorption peak of 490 nm, based on the absorbance spectrum of the formazan product produced after MTS reduction. The data read at 490 nm was subtracted by the data read at 630 nm, so as to subtract noise caused by cell debris and other non-specific absorbance values.

(5) The cell viability was calculated based on the absorbance value A, cell viability=(experimental group A/control group)×100%. The $IC_{50}$ value was calculated and dose-response curve was plotted.

The results are shown in FIG. 1, indicating that clofoctol specifically inhibits the cell activity of glioma stem cells.

Example 2: Lentivirus Infection of Eukaryotic Cells

Specific steps are as follows:

(1) Before infection, GSC2, U87MG SLC and HA cells were digested into single cell suspensions. After counting the cells, the cells were seeded at corresponding density ($1\times10^5$ to $3\times10^5$ cells/mL) in a 6-well cell culture plate with a system of 2 mL. GSC2 and U87MG SLC were allowed to grow naturally for 2 hours, and the HA cells were allowed to naturally grow until the cell adherence was obtained (about 4 hours);

(2) 2 μL lentivirus containing LV3 vector (bearing puromycin selection marker) labeled with green fluorescent was added into the culture medium of GSC2 cells, 2 μL lentivirus containing pLenti6 vector (bearing blasticidin selection marker, purchased from Promega) labeled with green fluorescence was added into the culture medium of U87MG SLC cells, and 2 μL lentivirus labeled with red fluorescence (without selection marker) was added into the culture medium of HA cell, respectively. After being mixed well, the cells were cultured overnight;

(3) The next morning, the virus-containing medium was removed and replaced with 2 mL of fresh medium, and the cells were allowed to grow naturally;

(4) At 48 hours to 72 hours, the cells were observed under a fluorescence microscope and detected whether there is a corresponding fluorescent expression to determine the success of infection;

(5) After confirming the fluorescent expression, the U87MG SLC cells stably expressing green fluorescence were screened with the corresponding concentration of blasticidin, the GSC2 cells stably expressing green fluorescence were screened with the corresponding concentration of puromycin, and HA cells stably expressing red fluorescence were screened by monoclonal screening method.

Figure 2A:
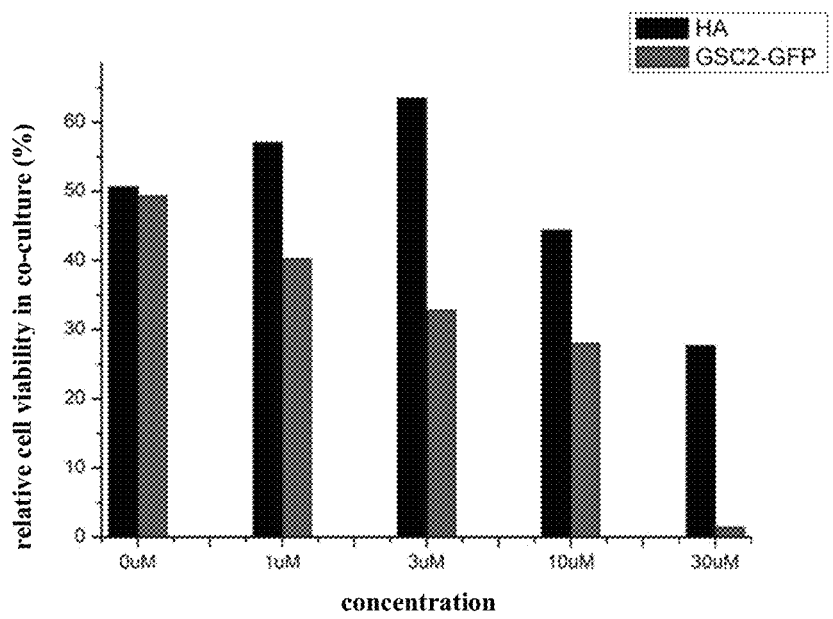
FIG. 2A and FIG. 2B: clofoctol specifically inhibits the glioma stem cells. GSC2-GFP (FIG. 2A) or U87MG SLC-GFP (FIG. 2B) labeled with green fluorescence was mixed with non-fluorescently-labeled HA in a system at a ratio of 1:1. After 24 hours of clofoctol treatment at the concentrations of 1 µM, 3 µM, 10 µM, 30 µM, flow cytometry was used to analyze the proportion of GSC2-GFP or U87MG SLC-GFP and HA in viable cells of different treatment groups. The relative cell viability of each cell component in the co-culture model was statistically analyzed by combining the cell viability of the co-culture model at different concentrations in different time periods.
Figure 2B:
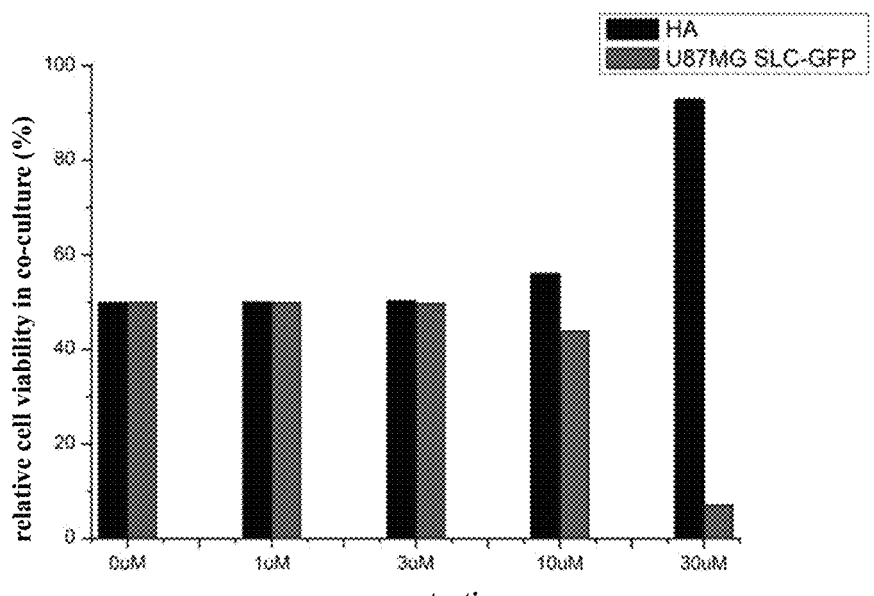
Figure 3A:
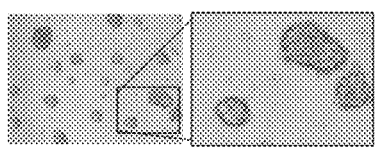
FIG. 3A to FIG. 3H: clofoctol inhibits the growth and maintenance of the tumorspheres of glioma stem cells. 100 µL single-cell suspension containing 5000 GSC2 was added to each well of a 96-well cell culture dish. After 4 days of natural growth, the original medium was removed, and 100 µL fresh medium containing various concentrations of the medicament was added to each well, the concentrations of the medicament were 0 µM (control, FIG. 3A), 0.03 µM (FIG. 3B), 0.1 µM (FIG. 3C), 0.3 µM (FIG. 3D), 1 µM (FIG. 3E), 3 µM (FIG. 3F), 10 µM (FIG. 3G), 30 µM (FIG. 3H), respectively. After 48 hours of treatment with medicament, the inhibition effect of clofoctol was detected using experiments in vitro representing the clinical formation of tumors from glioma stem cells. Clofoctol can significantly reduce the size and number of tumorspheres. At low concentrations (0.03 µM, 0.1 µM) of clofoctol, GSC2 can grow protuberances and exhibit clear differentiation-like characteristics. At high concentrations (10 µM, 30 µM) of clofoctol, clofoctol caused the death of marginal cells of tumorspheres, which extended throughout the whole tumorspheres.
Figure 3B:
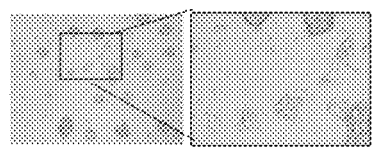
Figure 3C:
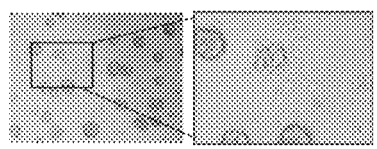
Figure 3D:
Figure 3E:
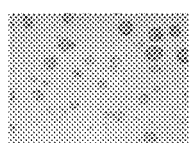
Figure 3F:
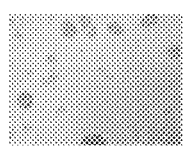
Figure 3G:
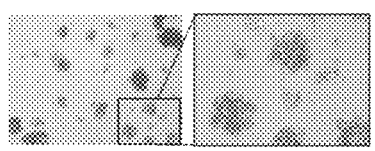
Figure 3H:
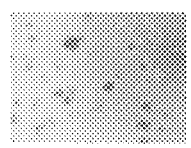
Figure 4:
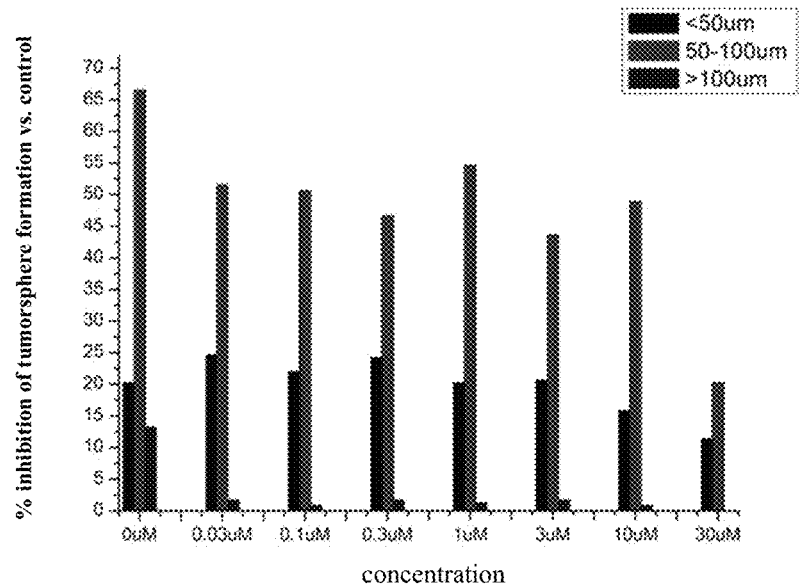
FIG. 4: statistical results of the experiments shown in FIGS. 3A to 3H.

Example 3: Flow Cytometry 6-well and 96-well cell culture plates were pre-coated with 100 μg/mL poly-lysine at 37° C. overnight, followed by washing twice with saline and allowing to air-dry. GSC2-GFP cells stably expressing green fluorescence and HA cells stably expressing red fluorescence were digested into single cell, and resuspended in fresh culture medium, counted and diluted to $5\times10^4$ cells/mL. Then, the two types of cells were mixed well at a ratio of 1:1, divided into five tubes. Clofoctol were added in each tube and mixed well, so that the concentrations of clofoctol were 0 μM, 1 μM, 3 μM, 10 μM, 30 μM, respectively. The resulting mixtures were added to a 6-well cell culture plate (2 mL) and a 96-well cell culture plate (100 μL, 3 replicate wells per group) respectively for 24 hours, before the MTS assay was used to detect the cell activity of each treatment group in the 96-well cell culture plate. The cells in the 6-well cell culture plates were collected separately, washed twice with PBS, and resuspended with 100 μL respectively. The proportion of GSC2-GFP and HA-RFP in the viable cells of each treatment group was analyzed by flow cytometry. Considering the changes in cell activity after medicament treatment of the co-culture model, the relative cell viability of each cell component in the co-culture model was statistically analyzed. The operations for the co-culture model—U87MG SLC-GFP+HA-RFP are as above;

The results are shown in FIGS. 2A and 2B, clofoctol specifically inhibits the cell activity of glioma stem cells in the co-culture model, when compared with normal human astrocytes.

Example 4: The Experiment of Tumorsphere Formation

After coating the 96-well cell culture dish, 100 µL single cell suspension containing 5000 GSC2 was added to each well. After 4 days of natural growth, the original medium was removed, and 100 µL fresh culture containing various concentrations of clofoctol was added to each well. The medicament concentrations were 0.03 µM, 0.1 µM, 0.3 µM, 1 µM, 3 µM, 10 µM and 30 µM, respectively. After 48 hours of medicament treatment, the morphological changes of the tumorspheres in each treatment group were observed under the microscope, and the number of tumorspheres in each treatment group was also counted.

The results are shown in FIGS. 3A to 3H and FIG. 4. The inhibition effect of clofoctol was detected using the experiments in vitro representing the clinical formation of tumors from glioma stem cells. It is found out that clofoctol can significantly reduce the size and number of tumorspheres. At low concentrations (0.03 µM, 0.1 µM) of clofoctol, GSC2 can grow protuberances and exhibit clear differentiation-like characteristics. At high concentrations (10 µM, 30 µM) of clofoctol, clofoctol caused the death of marginal cells of tumorspheres, which extend throughout the whole tumorspheres.

Example 5: Limited Dilution Experiment

Figure 5:
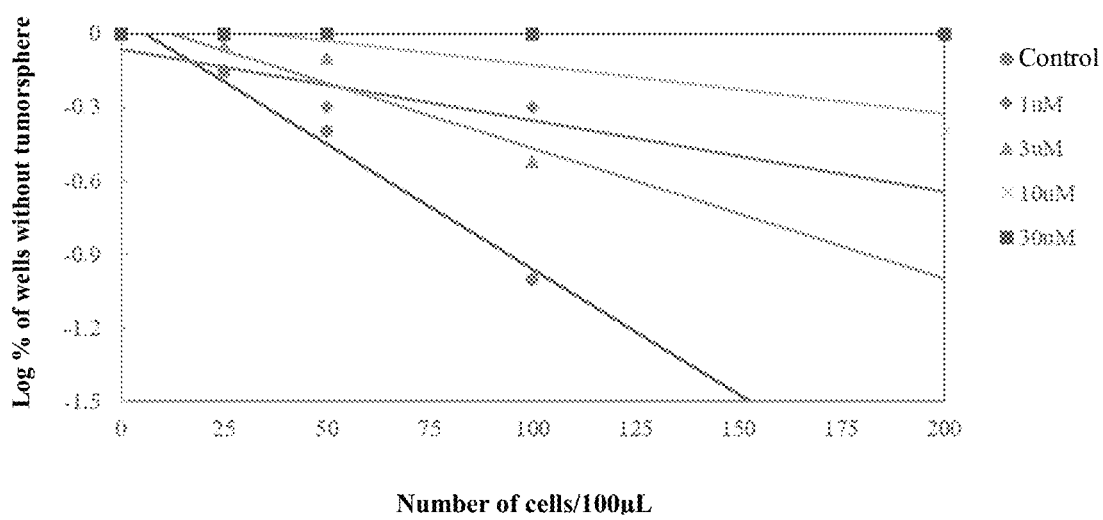
FIG. 5: clofoctol inhibits the self-renewal ability of glioma stem cells. GSC5 cells were diluted to 25, 50, 100, 200 cells/100 µL. The cells were treated with clofoctol at a concentration of 1 µM, 3 µM, 10 µM, 30 µM for 2 weeks, the percentage of the well without tumorsphere was then counted. The ordinate indicates the logarithm of the percentage of the well without tumorsphere.

The steps are as follows:
(1) The cells of GSC5 tumorspheres in suspension culture were collected into a 15 mL centrifuge tube, 0.5 mL of ACCUTASE enzyme (purchased from sigma) was added, and the cells were digested at 37° C. for 5 minutes. Then the cells were pipetted to single cell and the supernatant was removed after centrifugation;
(2) Fresh Neurobasal culture medium (purchased from gibco) was added. A portion of the cells were taken for trypan blue staining, followed by cell counting.
(3) After calculating the desired volume of cell culture medium, the cell concentration gradient of 200, 100, 50, 25 cells/well was set, and 10 replicate wells for each concentration were set. The DMSO control group and medicament treatment group with 0 µM, 1 µM, 3 µM and 10 µM of clofoctol were set.
(4) The cells were seeded in a 96-well plate at 100 and cultured in an incubator at 37° C., 5% $CO_2$, 2 weeks later the proportion of the well without tumorsphere was counted;

The results are shown in FIG. 5. Clofoctol significantly inhibits the formation of glioma stem cell clones at concentrations of 1 µM, 3 µM and 10 µM, i.e., it significantly inhibits the self-renewal ability of glioma stem cells.

Example 6: Recovery Assay (1) The 96-well cell culture plate was coated with 100 µg/mL poly-lysine.
(2) GSC5 was digested into single cell using ACCUTASE enzyme, resuspended in fresh Neurobasal culture medium, and the cells were then plated on the pre-coated 96-well cell culture plates overnight;

(3) clofoctol was added, the concentration of which were 0.03 µM, 0.1 µM, 0.3 µM, 1 µM, 3 µM, 10 µM and 30 µM, 9 replicate wells for each concentration;
(4) after 24 hours of treatment, 20 µL MTS/PMS mixed reagent was added to 3 replicate wells of each concentration to measure the cell activity. The medicament-containing medium in the other 6 replicate wells was removed, fresh medium was added to 3 of the 6 replicate wells, and medium containing the same concentration of clofoctol was added to the rest 3 replicate wells;
(5) after 48 hours of incubation, cell activity was detected by MTS assay.

After 48 hours of medicament treatment, the cells were restored for 48 hours and then detected, the steps are as above.

Figure 6A:
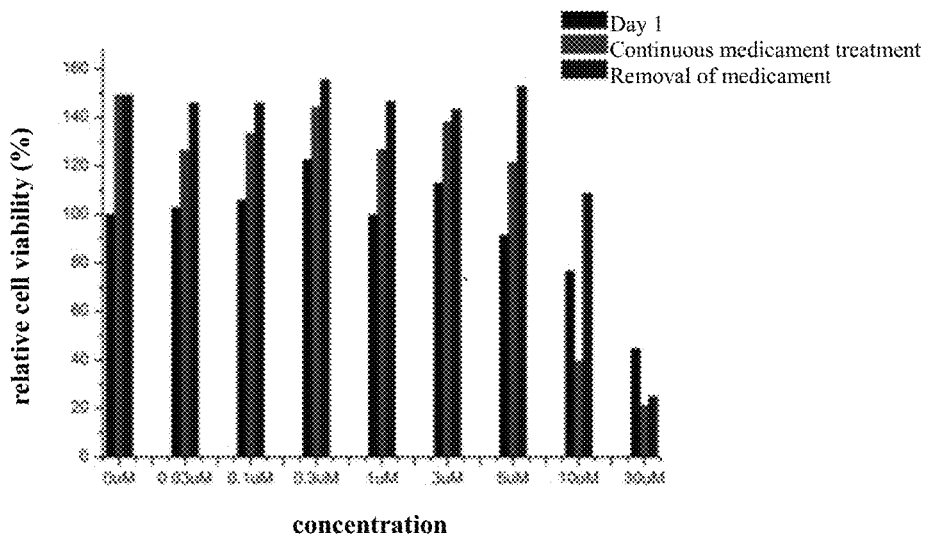
FIG. 6A and FIG. 6B: the effect of clofoctol on glioma stem cells is irreversible to some extent. GSC2 was treated with the medicament for 24 hours and 48 hours, and then the medicament was removed. The medium was replaced with fresh medium and the cells were cultured for another 48 hours. Then, the cell viability of each treatment group was measured by MTS assay, and was compared with the cell viability change observed in group receiving continuous medicament treatment. "Day 1" and "Day 2" indicate that MTS detection was performed after 24 hours or 48 hours of the medicament treatment. "continuous medicament treatment" means that the medicament is removed after 24 hours and 48 hours of treatment, and the fresh medium containing such medicament at corresponding concentration was added for another 48 hours of culture, and then MTS detection is performed. "Removal of medicament" means that the medicament is removed after 24 hours and 48 hours of treatment, and fresh medium without such medicament were added for another 48 hours of culture, and then MTS detection is performed.
Figure 6B:
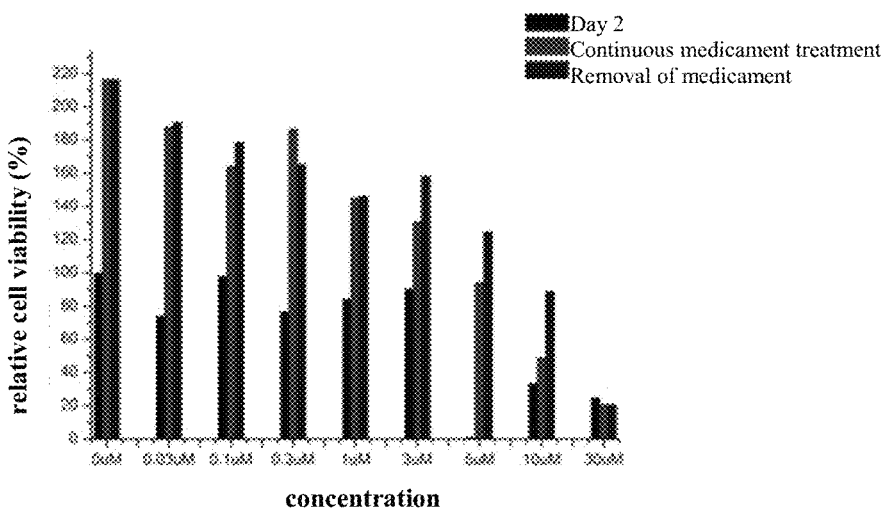

The results are shown in FIGS. 6A and 6B. The effect of clofoctol on glioma stem cells is irreversible to some extent.

Example 7: In Situ Tumorigenesis in Nude Mice

The cells were collected after 24 hours of pre-treatment with clofoctol at a concentration of 30 µM, washed twice with PBS, and a portion of the cells were subjected to trypan blue staining and cell counting. The cells were injected in situ into the intracranial striatum of Balb/C nude mice aged 5-7 weeks, at $10^5$ cells/mouse, 5 mice each group, and a DMSO control group was set.

Figure 7A:
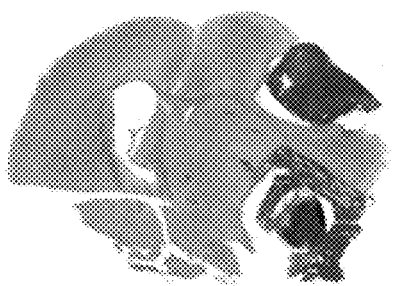
FIG. 7A and FIG. 7B: clofoctol can significantly inhibit the in situ tumorsphere formation ability in nude mice at a concentration of 30 µM. GSC2 was pretreated with clofoctol at a concentration of 30 µM for 24 hours, and then the viable cells were collected, and part of cells were subjected to trypan blue staining, and then the cells were counted. The cells were used for intracranial tumorigenesis, $10^5$ viable cells/mouse (5 nude mice). DMSO control group (5 nude mice), DMSO treatment group (FIG. 7A) and the clofoctol pretreatment group (FIG. 7B) were set. Once in situ tumorigenesis was observed in nude mice, HE staining was carried out.
Figure 7B:
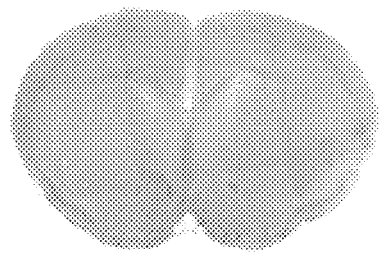

The results are shown in Table 1, FIG. 7A and FIG. 7B. The pretreatment of glioma stem cell GSC2 with clofoctol significantly inhibits its ability of in situ tumorigenesis in nude mice.

TABLE 1

| #cells (GSC2) | Control | clofoctol-30 µM |
|---|---|---|
| 1 * $10^5$ | 5/5 | 0/5 |

Example 8: The Experiment of Administration to Zebrafish Glioma Xenograft Model 3000 green-fluorescent-labeled U87MG SLC-GFP were injected into the yolk sac of the 48-hour zebrafish embryo. After 48 hours of natural growth, fluorescence microscopy was used to detect the tumorigenesis in zebrafish. And then clofoctol at a concentration of 10 µM was added to the zebrafish hatching solution. After 48 hours of medicament treatment, the green fluorescence intensity of zebrafish yolk sac was detected by fluorescence microscopy to determine the in vivo inhibitory effect of clofoctol on tumors in zebrafish xenograft models.

The results are shown in FIGS. 8A and 8B, which indicates that clofoctol significantly inhibits the in vivo tumor growth in a zebrafish xenograft model.

Example 9

Subcutaneous tumorigenesis at armpits of nude mice: after centrifugation and digestion, GSC2 single cell resuspended in PBS was subcutaneously inoculated into the armpits of 15 Balb/C nude mice of 5 weeks old. The inoculation number of the cells was $10^5$ cells/mouse. The tumor size of nude mice was recorded (tumor size in nude mice=length*width$^2$/2). When the subcutaneous tumors in nude mice reached about 100 mm$^3$, they were divided into DMSO group and clofoctol administration group. The dose administered was 20 mg/kg, the mice were administered by intraperitoneal injection for a period of 11 days. The changes in tumor size and the body weight in two groups of nude mice were recorded.

Figure 9B:
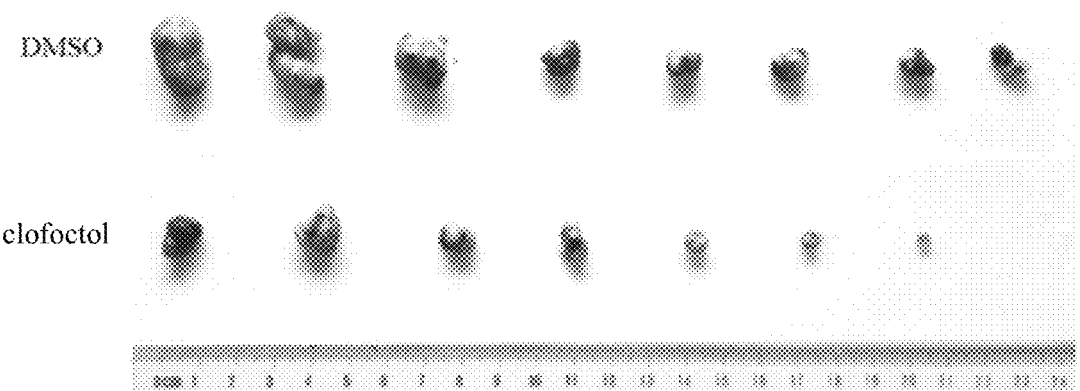
Figure 9C:
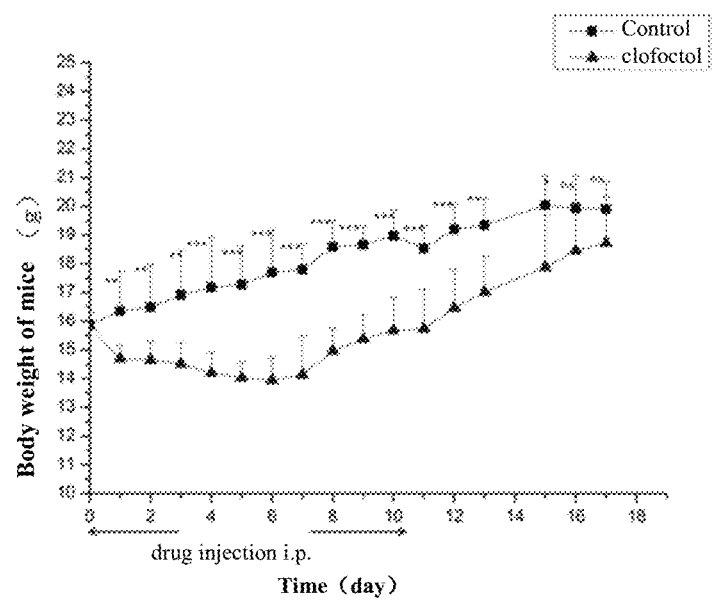
Figures 1, 10A:
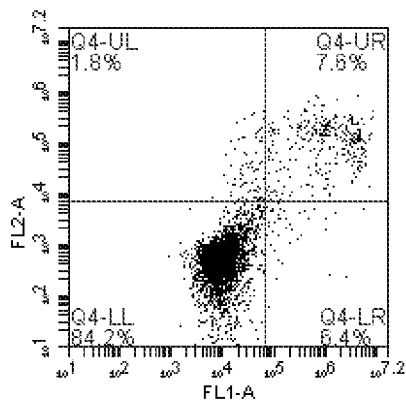
Figures 2, 10A:
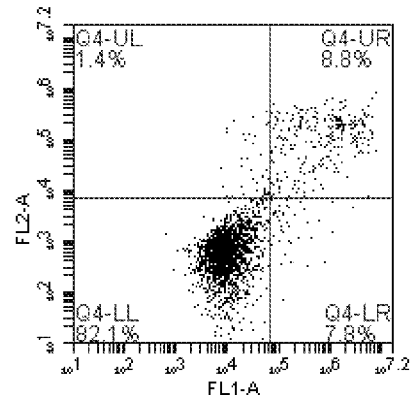
Figures 3, 10A:
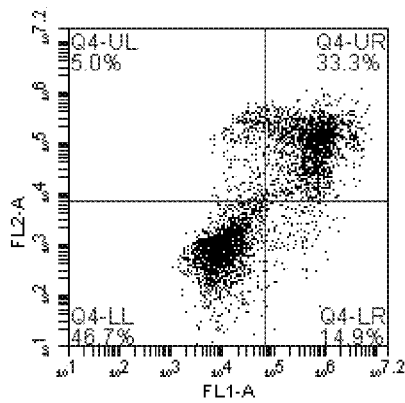
Figures 4, 10A:
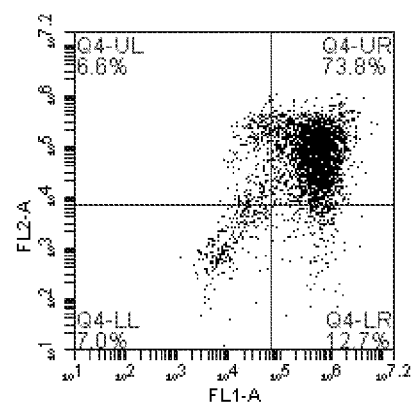
Figures 5, 10A:
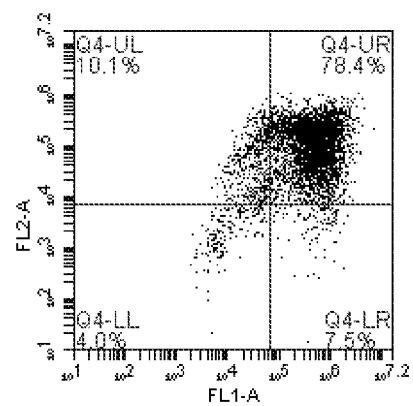
Figures 1, 10B:
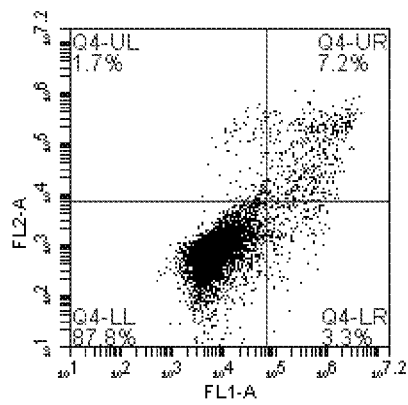
Figures 2, 10B:
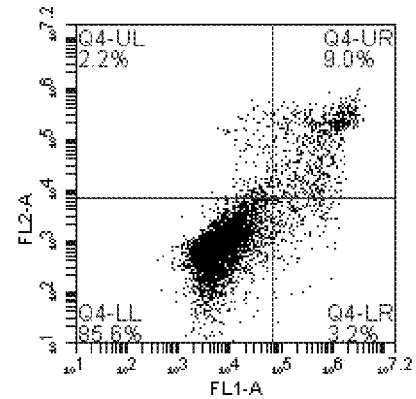
Figures 3, 10B:
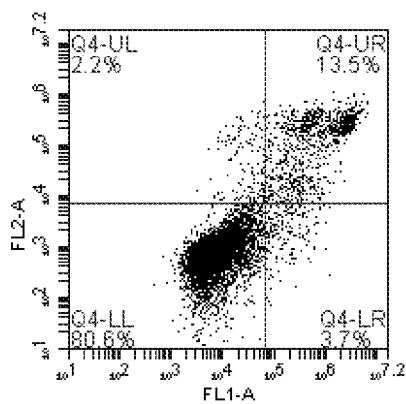
Figures 4, 10B:
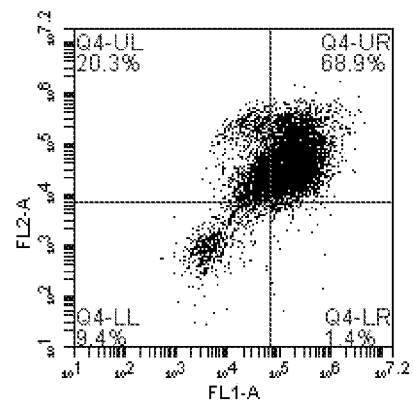
Figures 5, 10B:
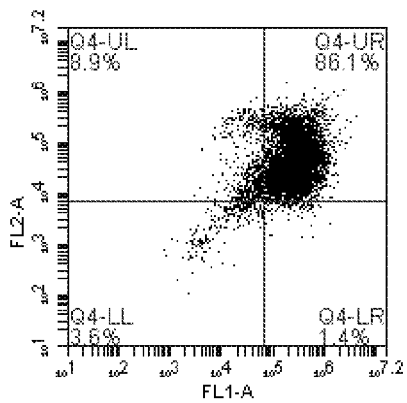

The results are shown in FIGS. 9A to 9C, clofoctol significantly inhibits tumor growth in the nude mouse xenograft model, and its side effects were small.

Example 10: Annexin V/PI Counterstaining for the Detection of Apoptosis

Specific steps are as follows:
(1) GSC2 were treated with clofoctol at the concentrations of 1 µM, 3 µM, 10 µM, 30 µM for 12 hours or 24 hours;
(2) the cells were collected and washed twice with PBS;
(3) the cells were resuspended with 50 µL 1*binding buffer with the cell density of about $1*10^6$ cells/mL;
(4) 2.5 µL FITC Annexin V and 2.5 µL PI were added;
(5) incubating for 15 min at room temperature in the darkness;
(6) 200 µL of 1*binding buffer was added to the system, and the cells in each treatment tube was passed through the cell strainer;
(7) flow cytometry analysis;

The Annexin V/PI counterstaining kit used was purchased from BD pharmingen with the product lot number 556547.

The results are shown in FIG. 10A-1 to FIG. 10B-5: clofoctol can induce apoptosis in glioma stem cells.

In summary, the present invention demonstrates that clofoctol has significant specific inhibitory effects on four glioma stem cell strains (U87MG SLC, U251 SLC, GSC2, GSC5) isolated in the laboratory at the cellular level (the $IC_{50}$ value after 48 hours treatment is 7.65 µM to 10.53 µM), when compared with glioma cells (U251, U87MG, N3 (primary glioma cells isolated from patient tumor tissue)), normal human astrocytes (HA), human embryonic kidney cells (293ET), human neural stem cells (H1P56NSC). Furthermore, it was confirmed by clone formation assay, inhibition of tumorsphere, and in situ tumorigenesis assay that clofoctol can significantly inhibit the ability of self-renewal, tumorsphere formation and tumorigenesis of glioma stem cells. Then, the present invention used a zebrafish glioma xenograft model and a nude mouse glioma subcutaneous xenograft model to demonstrate the therapeutic effect of clofoctol on glioma in vivo. Moreover, the present invention found out that clofoctol significantly induces apoptosis of glioma stem cells, which to some extent can explain the inhibitory effect of clofoctol on glioma stem cells and anti-tumor effect on glioma.

Therefore, the present invention for the first time discovered that the clinical medicament clofoctol can achieve the purpose of treating human neuroglioma by inhibiting human glioma stem cells. It is well known that small molecule compounds need to rely on related key groups to function in vivo. On such basis, even though modification occurred on other groups may produce different compounds, they still maintain their desired functions. Therefore, based on this, any modification to clofoctol still falls into the scope of present applicant and can be used in present applicant, as long as said modification achieves the same effect as that in present invention.

What is claimed is:

1. A method of treating human neuroglioma in a subject in need thereof, comprising administering clofoctol to the subject for the treatment of human neuroglioma.

2. The method of claim 1, wherein said human neuroglioma is treated by clofoctol through inhibiting the cell activity of glioma stem cells.

3. The method of claim 1, wherein said human neuroglioma is treated by clofoctol through inhibiting the capacities of glioma stem cells to self-renewal, formation of tumorsphere, and tumorigenesis in vivo.

4. The method of claim 1, wherein said human neuroglioma is treated by clofoctol through inducing the apoptosis of glioma stem cells.

5. The method of claim 2, wherein said glioma stem cells are selected from the group consisting of: U87MG SLC, U251 SLC, GSC2, and GSC5.

6. The method of claim 1, wherein said human neuroglioma is treated by clofoctol through inhibiting glioma cells.

7. The method of claim 6, wherein said glioma cells are selected from the group consisting of: U251, U87MG, and N3.

8. The method of claim 1, wherein said human neuroglioma is Grade I neuroglioma.

9. The method of claim 1, wherein said human neuroglioma is Grade II neuroglioma.

10. The method of claim 1, wherein said neuroglioma is Grade III neuroglioma.

11. The method of claim 1, wherein said neuroglioma is Grade IV neuroglioma.

12. The method of claim 3, wherein the glioma stem cells are selected from the group consisting of: U87MG SLC, U251 SLC, GSC2, and GSC5.

13. The method of claim 4, wherein the glioma stem cells are selected from the group consisting of: U87MG SLC, U251 SLC, GSC2, and GSC5.

14. The method of claim 1, wherein the subject is a human.

15. A method of inhibiting glioma stem cells, comprising contacting the glioma stem cells with clofoctol to induce apoptosis and/or inhibit cell activity, capacities of self-renewal, formation of tumorsphere, and/or tumorigenesis.

16. The method of claim 15, wherein the glioma stem cells are human glioma stem cells.

17. The method of claim 15, wherein the glioma stem cells are selected from the group consisting of: U87MG SLC, U251 SLC, GSC2, and GSC5.

18. A method of inhibiting glioma cells, comprising contacting the glioma cells with clofoctol to inhibit their activities.

19. The method of claim 18, wherein the glioma cells are human glioma cells.

20. The method of claim 18, wherein the glioma cells are selected from the group consisting of: U251, U87MG, and N3.

* * * * *